US006468559B1

(12) United States Patent
Chen et al.

(10) Patent No.: US 6,468,559 B1

(45) Date of Patent: Oct. 22, 2002

(54) ENTERIC COATED FORMULATION OF BISHOSPHONIC ACID COMPOUNDS AND ASSOCIATED THERAPEUTIC METHODS

(75) Inventors: Feng-Jing Chen, Salt Lake City, UT (US); Mahesh V. Patel, Salt Lake City, UT (US)

(73) Assignee: Lipocine, Inc., Salt Lake City, UT (US)

( * ) Notice: Subject to any disclaimer, the term of this patent is extended or adjusted under 35 U.S.C. 154(b) by 0 days.

(21) Appl. No.: 09/561,489

(22) Filed: Apr. 28, 2000

(51) Int. Cl.[7] .................................................. A61K 9/48

(52) U.S. Cl. ....................... 424/451; 424/456; 424/457; 424/458; 424/459; 424/463; 424/496; 424/498; 424/502; 424/460; 424/461; 424/462; 514/102; 514/104; 514/108; 514/962

(58) Field of Search ................................ 424/451, 456, 424/457, 458, 459, 463, 496, 498, 502, 460, 461, 462; 514/108, 102, 104, 962

(56) References Cited

U.S. PATENT DOCUMENTS 4,621,077 A 11/1986 Rosini et al.
4,627,850 A 12/1986 Deters et al.
5,227,506 A * 7/1993 Saari et al. ................. 514/108
5,358,941 A 10/1994 Bechard et al.
5,413,572 A 5/1995 Wong et al.
5,431,920 A 7/1995 Bechard
5,462,932 A 10/1995 Brenner et al.
5,622,721 A 4/1997 Dansereau et al.
5,681,590 A 10/1997 Bechard et al.
5,882,656 A 3/1999 Bechard et al.
5,935,602 A 8/1999 Dansereau et al.
6,015,801 A 1/2000 Daifotis et al.

FOREIGN PATENT DOCUMENTS

WO WO 93/09785 5/1993

* cited by examiner

*Primary Examiner*—Thurman K. Page
*Assistant Examiner*—Lakshmi Channavajjala
(74) *Attorney, Agent, or Firm*—Reed & Associates; Dianne E. Reed

(57) ABSTRACT

Oral dosage forms are provided for the administration of a bisphosphonic acid compound in the prevention and treatment of conditions involving calcium or phosphate metabolism, i.e., conditions associated with bone resorption such as osteoporosis, Paget's disease, periprosthetic bone loss, osteolysis, malignant hypercalcemia, metastatic bone disease, multiple myeloma, and periodontal disease. The dosage forms are either enterically coated capsules housing the drug in a liquid or semi-solid carrier, or enterically coated osmotically activated drug delivery devices.

59 Claims, No Drawings

ENTERIC COATED FORMULATION OF BISHOSPHONIC ACID COMPOUNDS AND ASSOCIATED THERAPEUTIC METHODS

TECHNICAL FIELD

The present invention relates generally to drug delivery, and more specifically relates to novel enteric coated pharmaceutical dosage forms that for oral administration of bisphosphonic acid compounds. The invention additionally relates to methods for administering a bisphosphonic acid compound using the novel dosage forms.

BACKGROUND

A number of bisphosphonic acids are known as pharmaceutical agents, particularly in the diagnosis and treatment of disorders and conditions related to bone resorption, calcium metabolism and phosphate metabolism. Such disorders and conditions include, for example, osteoporosis, Paget's disease, periprosthetic bone loss or osteolysis, metastatic bone disease, hypercalcemia of malignancy, multiple myeloma, periodontal disease, and tooth loss. The bisphosphonic acids, or "bisphosphonates," which are known to be useful in treating such disorders and conditions fall into three categories: a first generation of drugs, including etidronate, which have significant activity but do not reliably suppress bone resorption, and result in undesirable side effects (etidronate, for example, can give rise to osteomalacia, resulting in a decrease in bone mineralization; see Boyce et al. (1984) *Lancet* 1(8381):821–824, and Gibbs et al. (1986) *Br. Med. J.* 2:1227–1229); a second generation of drugs, e.g., pamidronate, which reliably suppress bone resorption when administered parenterally, but are not orally active; and a third generation of drugs typified by alendronate and risedronate, that exhibit both oral and parenteral efficacy.

The known bisphosphonic acids include 1-hydroxyethane-1,1-diphosphonic acid (etidronic acid, salts of which are referred to as "etidronate"), 1,1-dichloromethylene-1,1-bisphosphonic acid (clodronic acid, salts of which are is referred to as "clodronate"), 3-amino-1-hydroxypropylidene-1,1-bisphosphonic acid (pamidronic acid, salts of which are referred to as "pamidronate"), 4-amino-1-hydroxybutylidene-1,1-bisphosphonic acid (alendronic acid, salts of which are referred to as "alendronate), 6-amino-1-hydroxy-hexylidene-1,1-bisphosphonic acid (neridronic acid, salts of which are referred to as "neridronate"), (4-chlorophenyl)-thiomethane-1,1-diphosphonic acid (tiludronic acid, salts of which are referred to as "tiludronate"), 2-(3-pyridinyl)-1-hydroxy-2-(3-pyridinyl)-ethylidene-1,1-bisphosphonic acid (risedronic acid, salts of which are referred to as "residronate"), cycloheptylaminomethylene-1,1-bisphosphonic acid (cimadronic acid, salts of which are referred to as "cimadronate"), 1-hydroxy-3-(N-methyl-N-pentylamino)-propylidene-1,1-bisphosphonic acid (ibandronic acid, salts of which are referred to as "ibandronate"), 3-(dimethylamino)-1-hydroxypropylidene-1,1-bisphosphonic acid (olpadronic acid, salts of which are referred to as "olpadronate"), [2-(2-pyridinyl)-ethylidene]-1,1-bisphosphonic acid (piridronic acid, salts of which are referred to as "piridronate") and 1-hydroxy-2-(1H-imidazol-1-yl)ethylidene-1,1-bisphosphonic acid (zoledronic acid, salts of which are referred to as "zoledronate"). Although the bisphosphonic acids are therapeutically effective, oral administration of the drugs is problematic, primarily because of adverse gastrointestinal effects, particularly irritation of the esophagus. Pamidronate has been associated with esophageal ulcers, as has alendronate, although to a lesser extent. See, for example, Lufkin et al. (1994) *Osteoporosis International* 4:320–322; De Groen et al. (1996), *N. Eng. J. Med.* 335(124):1016–1021; Castell et al. (1996) *N. Eng. J. Med.* 335(124):1058–1059; and Lieberman et al. (1996) *N. Eng. J. Med.* 3(124):1069–1070. Even with risedronate, which because of its potency can be administered at relatively low doses, complaints such as heartburn and esophageal burning are frequent.

Although efforts have been made to reduce the adverse gastrointestinal effects of bisphosphonic acids, there is a continuing need for dosage forms containing these active agents wherein undesirable side effects are minimnized and patient compliance and thus therapeutic efficacy are improved.

The following references pertain to one or more aspects of the invention and may provide useful background information:

U.S. Pat. No. 4,621,077 to Rosini et al. describe biphosphonic acids as therapeutic agents, the acids including alendronate, difluoromethanebiphosphonic acid, and 5-amino-1-hydroxypentane-1,1-biphosphonic acid. U.S. Pat. Nos. 5,358,941 and 5,681,590 to Bechard et al. describe immediate release tablets of bisphosphonic acids and salts thereof, for the treatment of disturbances involving calcium or phosphate metabolism, e.g., treatment and prevention of diseases involving bone resorption, particularly osteoporosis, Paget's disease, malignant hypercalcemia and metastatic bone disease.

International Patent Publication WO 93/09785, U.S. Pat. No. 5,622,721 to Dansereau et al., and U.S. Pat. No. 5,935,602 to Dansereau et al. disclose enterically coated dosage forms of the drug risedronate. The '602 patent describes delayed release risedronate formulations comprised of compressed tablets that are enterically coated, compressed tablets that contain enterically coated drug particles, or capsules containing enterically coated drug particles. U.S. Pat. No. 5,431,920 to Bechard describes an enterically coated dosage form comprising a core tablet containing a therapeutically effective amount of a bisphosphonic active agent, a stability-enhancing subcoat designed to minimize migration of active agent from the core tablet to the surface of the enteric coating, and an enteric film formulated to rapidly and completely dissolve once the dosage form enters the proximal portion of the lower gastrointestinal tract. U.S. Pat. No. 6,015,801 to Daifotis et al. pertains to a method for administering a bisphosphonic acid compound while minimizing gastrointestinal side effects, the method involving administering a high unit dosage of the active agent at relatively infrequent dosing intervals, e.g., on a once-weekly or biweekly basis.

U.S. Pat. No. 5,462,932 to Brenner et al. describes an oral alendronate formulation in the form of a liquid, for administration to individuals who have difficult in swallowing tablets and other solid dosage forms.

U.S. Pat. No. 4,627,850 to Deters et al. and U.S. Pat. No. 5,413,572 to Wong et al. pertain to osmotic dosage forms in which a drug-containing composition is contained within a semipermeable outer wall, i.e., a membrane that is permeable to the passage of fluid, is impermeable to any influx of drug, and contains an orifice that allows delivery of the drug-containing composition from the capsule.

SUMMARY OF THE INVENTION

Accordingly, it is a primary object of the invention to address the above-mentioned need in the art by providing an enterically coated dosage form for the administration of a bisphosphonic acid compound.

It is another object of the invention to provide such a dosage form comprised of a capsule housing the drug in a liquid or semi-solid carrier.

It is still another object of the invention to provide such a dosage form comprised of an osmotically activated device in which a semipermeable membrane encapsulates a drug-containing formulation.

It is an additional object of the invention to provide a method for treating an individual having a condition that is responsive to administration of a bisphosphonic acid compound, by administering a dosage form as provided herein within the context of an effective dosing regimen.

Additional objects, advantages and novel features of the invention will be set forth in part in the description which follows, and in part will become apparent to those skilled in the art upon examination of the following, or may be learned by practice of the invention.

In one aspect of the invention, then, a pharmaceutical formulation for oral administration is provided which comprises an enterically coated capsule housing a therapeutically effective amount of an active agent selected from bisphosphonic acids and pharmacologically acceptable salts, hydrates, and other derivatives thereof, in a pharmaceutically acceptable liquid or semi-solid carrier. Generally, the bisphosphonic acid compound has the structure of formula (I)

(I)

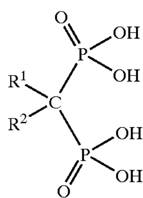

wherein $R^1$ is selected from the group consisting of hydrido, hydroxyl, alkoxy and halo, and $R^2$ is selected from the group consisting of halo, $-(CH_2)_m-NR^3R^4$, $-(CH_2)_n-R^5$, $-O-R^6$ and $-S-R^7$ wherein m is an integer in the range of zero to 8 inclusive, n is an integer in the range of 1 to 4 inclusive, $R^3$ and $R^4$ are independently hydrido or alkyl, or together form a $C_5$–$C_7$ cyclic group, and $R^5$, $R^6$ and $R^7$ are independently aryl (including heteroaryl) and may be either unsubstituted or substituted with one or more substituents, e.g., halo, particularly chloro. The carrier is a substantially nonaqueous liquid or semi-solid in which the active agent is dissolved or suspended, and may be a solvent, an oil or triglyceride, a surfactant, or a combination thereof.

In another aspect of the invention, a pharmaceutical formulation for oral administration of a bisphosphonic acid compound is provided which comprises an enterically coated, osmotically activated device in the form of a semipermeable membrane housing a drug-containing formulation which may or may not be liquid or semi-solid as described above. The membrane is permeable to water but impermeable to the drug, and is provided with an orifice through which drug is released as water flows into the device. The drug typically has the structure of formula (I), and the carrier is as described above with respect to the enterically coated capsules.

The enteric coating protects the upper gastrointestinal tract, increases the extent and/or consistency of drug absorption, reduces the effect of food on drug absorption, and also makes swallowing easier. In some cases, drug absorption may be increased quite significantly relative to conventional dosage forms, such that the active agent may be administered only once every two to twelve weeks without any decrease in therapeutic efficacy.

In still another aspect of the invention, a method is provided for treating a patient having a condition that is responsive to administration of an active agent selected from bisphosphonic acids and pharmacologically acceptable salts, hydrates and other derivatives thereof, the method comprising orally administering to the patient, within the context of an effective dosing regimen, a pharmaceutical formulation as described above, i.e., an enterically coated capsule or an enterically coated, osmotically activated device. The condition generally involves calcium or phosphate metabolism, i.e., conditions associated with bone resorption such as osteoporosis, Paget's disease, periprosthetic bone loss, osteolysis, malignant hypercalcemia, metastatic bone disease, multiple myeloma, and periodontal disease.

DETAILED DESCRIPTION OF THE INVENTION

I. Definitions and Nomenclature

Before the present formulations and methods of use are disclosed and described, it is to be understood that unless otherwise indicated this invention is not limited to specific pharmacologically active agents, specific pharmaceutical carriers, or to particular administration regimens, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an active agent" includes a single active agent or mixtures of active agents, reference to "a pharmaceutical carrier" includes a single carrier or combinations of two or more carriers, reference to "a coating" refers to a single coating or layers of multiple coatings, and the like.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not.

The terms "active agent," "drug" and "pharmacologically active agent" are used interchangeably herein to refer to a chemical material or compound which, when administered to an organism (human or animal, generally human) induces a desired pharmacologic effect. In the context of the present invention, the terms refer to a compound that is capable of being delivered orally.

The term "bisphosphonic acid" as used herein refers to a compound having the structure of formula (I), below, or to a pharmaceutically acceptable salt, hydrate, ester, anhydride, carbamate, amide thereof.

By the terms "effective amount" or "pharmaceutically effective amount" of an agent as provided herein are meant a nontoxic but sufficient amount of the agent to provide the desired therapeutic effect. As will be pointed out below, the exact amount required will vary from subject to subject, depending on age, general condition of the subject, the severity of the condition being treated, and the particular active agent administered, and the like. An appropriate "effective" amount in any individual case may be determined by one of ordinary skill in the art by reference to the pertinent texts and literature and/or using routine experimentation.

By "pharmaceutically acceptable" carrier is meant a carrier comprised of a material that is not biologically or otherwise undesirable. The term "carrier" is used generically herein to refer to any components present in the pharmaceutical formulations other than the active agent or agents, and thus includes diluents, binders, lubricants, disintegrants, fillers, coloring agents, wetting or emulsifying agents, pH buffering agents, preservatives, and the like.

Similarly, a "pharmaceutically acceptable" salt or a "pharmaceutically acceptable" derivative of a compound as provided herein is a salt or other derivative which is not biologically or otherwise undesirable.

The term "controlled release" is intended to refer to any drug-containing formulation in which the manner and profile of drug release from the formulation are controlled. The term "controlled release" refers to immediate as well as nonimmediate release formulations, with nonimmediate release formulations including but not limited to sustained release and delayed release formulations.

The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between oral administration of the formulation and the release of the drug therefrom. "Delayed release" may or may not involve gradual release of drug over an extended period of time, and thus may or may not be "sustained release." The "delayed release" formulations herein are enterically coated compositions. "Enteric coating" or "enterically coated" as used herein relates to the presence of polymeric materials in a drug formulation that results in an increase in the dosage form's resistance to degradation in the upper gastrointestinal tract, and/or a decrease in the release or exposure of the drug in the upper gastrointestinal tract.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, the present method of "treating" osteoporosis, as the term "treating" is used herein, encompasses both prevention of osteoporosis in a predisposed individual and treatment of osteoporosis in a clinically symptomatic individual.

The following definitions pertain to chemical structures, molecular segments and substituents:

The term "alkyl" as used herein refers to a branched or unbranched saturated hydrocarbon group of 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. The term "lower alkyl" intends an alkyl group of 1 to 6 carbon atoms, preferably 1 to 4 carbon atoms.

The term "alkoxy" as used herein intends an alkyl group bound through a single, terminal ether linkage; that is, an "alkoxy" group may be defined as -O-alkyl where alkyl is as defined above. A "lower alkoxy" group intends an alkoxy group containing one to six, more preferably one to four, carbon atoms.

The term "aryl" as used herein, and unless otherwise specified, refers to an aromatic species containing at least 1, and preferably 1 to 5 aromatic rings, either fused or linked, and either unsubstituted or substituted with 1 or more substituents typically selected from the group consisting of lower alkyl, lower alkoxy, halogen, and the like. Heteroatoms may be present, in which case the "aryl" group is "heteroaromatic." Preferred aryl substituents contain 1 aromatic ring or 2 or 3 fused or linked aromatic rings.

The terms "halo" and "halogen" are used in the conventional sense to refer to a chloro, bromo, fluoro or iodo substituent. Preferred halo substituents herein are chloro.

II. The Novel Formulations

In a first embodiment, the invention features pharmaceutical dosage forms that provide for controlled release of a bisphosphonic acid compound such as alendronic acid. The dosage forms are enterically coated (a) capsules housing a bisphosphonic acid or salt or hydrate thereof in a pharmaceutically acceptable liquid or semi-solid carrier, and (b) osmotically activated drug delivery devices. The bisphosphonic acid compound generally although not necessarily has the structure of formula (I)

(I)

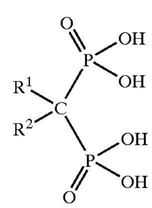

wherein $R^1$ is selected from the group consisting of hydrido, hydroxyl, alkoxy and halo, and $R^2$ is selected from the group consisting of halo, —$(CH_2)_m$—$NR^3R^4$, —$(CH_2)_n$—$R^5$, —O—$R^6$ and —S—$R^7$ wherein m is an integer in the range of zero to 8 inclusive, n is an integer in the range of 1 to 4 inclusive, $R^3$ and $R^4$ are independently hydrido or alkyl, or together form a $C_5$–$C_7$ cyclic group, and $R^5$, $R^6$ and $R^7$ are independently aryl (including heteroaryl) and may be either unsubstituted or substituted with one or more substituents, e.g., halo, particularly chloro.

In preferred bisphosphonic acid compounds, $R^1$ is selected from the group consisting of hydrido, hydroxyl and halo, and $R^2$ is selected from the group consisting of halo, —$(CH_2)_m$—$NR^3R^4$, —$(CH_2)_n$—$R^5$ wherein $R^5$ is imidazolyl or pyridinyl, and —S—$R^7$ wherein $R^7$ is 4-chlorophenyl.

Examples of such bisphosphonic acids include 1-hydroxyethane-1,1-diphosphonic acid (etidronic acid), 1,1-dichloromethylene-1,1-bisphosphonic acid (clodronic acid), 3-amino-1-hydroxypropylidene-1,1-bisphosphonic acid (paamidronic acid), 4-amino-1-hydroxybutylidene-1,1-bisphosphonic acid (alendronic acid), 6-amino-1-hydroxyhexylidene-1,1-bisphosphonic acid (neridronic acid), (4-chlorophenyl)thio-methane-1,1-diphosphonic acid (tiludronic acid), 1-hydroxy-2-(3-pyridinyl)-ethylidene-1,1-bisphosphonic acid (risedronic acid), cycloheptylaminomethylene-1,1-bisphosphonic acid (cimadronic acid), 1-hydroxy-3-(N-methyl-N-pentylamino) propylidene-1,1-bisphosphonic acid (ibandronic acid), 3-(dimethylamino)-1-hydroxypropylidene-1,1- bisphosphonic acid (olpadronic acid), [2-(2-pyridinyl) ethylidene]-1,1-bisphosphonic acid (piridronic acid) and 1-hydroxy-2-(1H-imidazol-1-yl)ethylidene-1,1-bisphosphonic acid (zoledronic acid). Alendronate (4-amino-1-hydroxy-butylidene-1,1-bisphosphonic acid monosodium salt trihydrate), risedronate, tiludronate, and zoledronate are preferred compounds for administration using the present dosage forms.

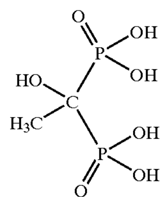

etidronic acid

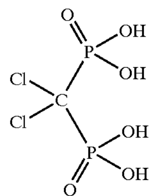

clodronic acid

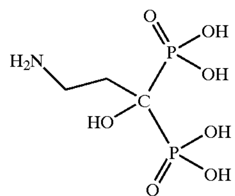

pamidronic acid

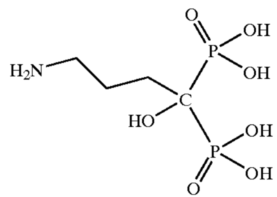

alendronic acid

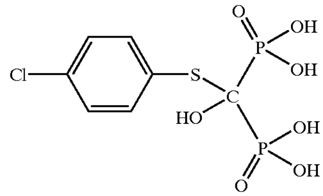

tiludronic acid

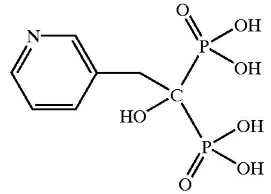

risedronic acid

-continued

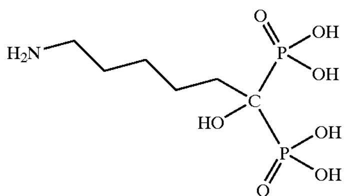

neridronic acid

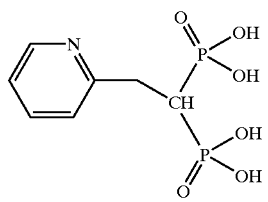

piridronic acid

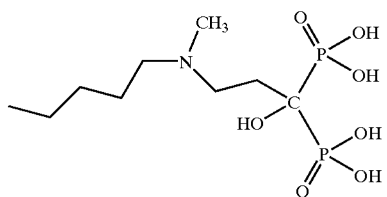

ibandronic acid

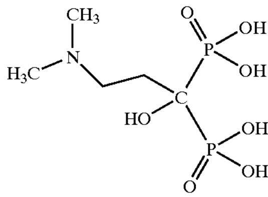

olpadronic acid

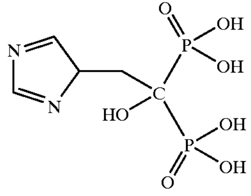

zoledronic acid

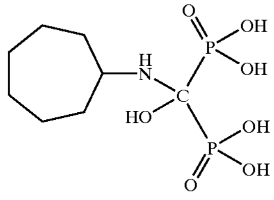

cimadronic acid

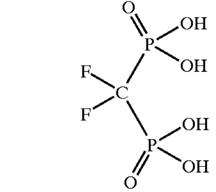

2,2-difluoro analog of clodronic acid

-continued

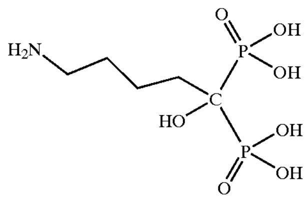

5-amino-1-hydroxypentane-1,1-bisphosphonic acid

The bisphosphonic acid compound may be in crystalline or amorphous form, and mixtures of bisphosphonic acids may be employed. The bisphosphonic acid may also be in the form of a pharmaceutically acceptable salt, ester, anhydride, carbamate, amide, hydrate, or other analog, derivative or prodrug, or a combination thereof (e.g., a sodium salt trihydrate, as in alendronate). Salts of the bisphosphonic acid compounds may be obtained commercially or can be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, amino acids, and the like, as well as inorganic acids, e.g., hydrochloric acid, hydrobromic acid, sulfuric acid, nitric acid, phosphoric acid, and the like. Basic salts of acid moieties, e.g., phosphonic acid groups, may be prepared using a pharmaceutically acceptable base. Salts formed with the phosphonic acid group include, but are not limited to, alkali metal salts, alkaline earth metal salts and organic base salts. For example, bases such as sodium hydroxide, potassium hydroxide, ammonium hydroxide, calcium hydroxide, magnesium hydroxide, trimethylamine, lysine, arginine, triethanolamine, and the like, may be used. Preparation of esters involves functionalization of hydroxyl and/or carboxyl groups which may be present. These esters are typically acyl-substituted derivatives of free alcohol groups, i.e., moieties which are derived from carboxylic acids of the formula RCOOH where R is alkyl, and preferably is lower alkyl. Pharmaceutically acceptable esters may be prepared using methods known to those skilled in the art and/or described in the pertinent literature. Anhydrides, carbamates, amides, hydrates, and other analogs, derivatives and prodrugs can be readily prepared as well, using conventional means, and incorporated into the present formulations.

A. Enterically Coated Capsules

The encapsulated formulation comprises a bisphosphonic acid compound as above dispersed in a pharmaceutically acceptable carrier that is either liquid or semi-solid. The carrier acts as a dispersing medium for the active agent, so that the bisphosphonic acid compound is solubilized or suspended therein. Generally, the carrier is (a) a solvent, (b) an oil or triglyceride, (c) a surfactant, or a mixture thereof Solvents are generally selected from the following groups: (1) aqueous media, including water and aqueous buffers; (2) alcohols and polyols, such as ethanol, isopropanol, butanol, benzyl alcohol, ethylene glycol, propylene glycol, butanediols and isomers thereof, glycerol, pentaerythritol, sorbitol, mannitol, diethylene glycol monoethyl ether (available under the trademark Transcutol), diethylene glycol monomethyl ether, dimethyl isosorbide, polyethylene glycol (PEG), polypropylene glycol, polyvinylalcohol, hydroxypropyl methylcellulose and other cellulose derivatives, cyclodextrins and cyclodextrin derivatives such as hydroxypropyl cyclodextrins; (3) ethers, such as dimethyl isosorbide, and ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide); (4) amides such as 2-pyrrolidone, 2-piperidone, caprolactam, N-alkyl-pyrrolidones (e.g., N-methylpyrrolidone), N-hydroxyalkyl-pyrrolidone (e.g., N-hydroxyethylpyrrolidone), N-alkylpiperidones, N-alkylcaprolactams, dimethylacetamide, and polyvinylpyrrolidone; and (5) esters such as ethyl propionate, tributylcitrate, acetyl triethylcitrate, acetyl tributylcitrate, triethylcitrate, ethyl oleate, ethyl caprylate, ethyl butyrate, triacetin, monooctanoin, propylene glycol monoacetate, propylene glycol diacetate, caprolactone and isomers thereof, valerolactone and isomers thereof, and butyrolactone and isomers thereof.

Preferred solvents include water, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol (particularly polyethylene glycol having a molecular weight in the range of about 200 to 1000), glycofurol, diethylene glycol monoethyl ether, propylene glycol, sorbitol, glycerol, ethanol and dimethyl isosorbide. Particularly preferred solvents within this group are sorbitol, glycerol, triacetin, ethanol, PEG 400, glycofurol and propylene glycol.

The amount of solvent or solvents that can be included in a single dosage form is not particularly limited. Of course, when the dosage form is administered to a patient, the amount of a given solvent is limited to a bioacceptable amount, which is readily determined by one of skill in the art. In some circumstances, it may be advantageous to include excess amounts of solvents, for example, to facilitate the dispersing process of the active agent or to optimize the concentration thereof. The excess solvent may be removed prior to administration to a patient using appropriate techniques, such as extraction, filtration, evaporation, distillation, spray drying, lyophilization, and the like.

As noted above, the carrier can also comprise one or more pharmaceutically acceptable oils or triglycerides. In general, suitable oils and triglycerides are readily available from commercial sources. Examples of specific oils and triglycerides include, but are not limited to, the following: aceituno oil; almond oil (particularly super refined almond oil, from Croda); arachis oil; babassu oil; blackcurrant seed oil; borage oil; buffalo ground oil; candlenut oil; canola oil (e.g., Lipex 108, from Abitec); castor oil; Chinese vegetable tallow oil; cocoa butter; coconut oil (e.g., Pureco 76, from Abitec); coffee seed oil; corn oil (particularly super refined corn oil, from Croda); cottonseed oil (particularly super refined cottonseed oil, from Croda); crambe oil; cuphea species oil; evening primrose oil; grapeseed oil; groundnut oil; hemp seed oil; illipe butter; kapok seed oil; linseed oil; menhaden oil (particularly super refined menhaden oil, from Croda); mowrah butter; mustard seed oil; oiticica oil; olive oil (particularly super refined olive oil, from Croda); palm oil; palm kernel oil; peanut oil (particularly super refined peanut oil, from Croda); poppy seed oil; rapeseed oil; rice bran oil; safflower oil (particularly super refined safflower oil, from Croda); sal fat; sesame oil (particularly super refined sesame oil, from Croda); shark liver oil (particularly super refined shark liver oil, from Croda); shea nut oil; soybean oil (particularly super refined soybean oil, from Croda); stillingia oil; sunflower oil; tall oil; tea seed oil; tobacco seed oil; tung oil (China wood oil); ucuhuba oil; vernonia oil; wheat germ oil (particularly super refined wheat germ oil, from Croda); hydrogenated castor oil (e.g., Castorwax); hydrogenated coconut oil (e.g., Pureco 100, from Abitec); hydrogenated cottonseed oil (e.g., Dritex C, from Abitec); hydrogenated palm oil (e.g., Dritex PST, from Abitec; Softisan 154, from Huils); hydrogenated soybean oil(e.g., Sterotex HM NF or Dritex S, from Abitec); hydrogenated vegetable oil (e.g., Sterotex NF or Hydrokote M, from Abitec); hydrogenated cottonseed and castor oil (e.g., Sterotex K, from Abitec); partially hydrogenated soybean oil (e.g., Hydrokote AP5, from Abitec); partially hydrogenated soy and cottonseed oil (e.g., Apex B, from Abitec); glyceryl tributyrate; glyceryl tricaproate; glyceryl tricaprylate; glyceryl tricaprate (e.g., Captex 1000, from Abitec); glyceryl triundecanoate (e.g., Captex 8227, from Abitec); glyceryl trilaurate; glyceryl trimyristate (e.g., Dynasan 114, from Huils); glyceryl tripalmitate (e.g., Dynasan 116, from Hüls); glyceryl tristearate (e.g., Dynasan 118, from Hüls); glyceryl triarchidate; glyceryl trimyristoleate; glyceryl tripalmitoleate; glyceryl trioleate; glyceryl trilinoleate; glyceryl trilinolenate; glyceryl tricaprylate/caprate (e.g., Captex 300 or 355, from Abitec, Miglyol 810 or 812, from Huils); glyceryl tricaprylate/caprate/laurate (e.g., Captex 350, from Abitec); glyceryl tricaprylate/caprate/linoleate (e.g., Captex 810, from Abitec, Miglyol 818, from Hüls); glyceryl tricaprylate/caprate/stearate (e.g., Softisan 378, from Hüls); glyceryl tricaprylate/laurate/stearate; glyceryl 1,2-caprylate-3-linoleate; glyceryl 1,2-caprate-3-stearate; glyceryl 1,2-laurate-3-myristate; glyceryl 1,2-myristate-3-laurate; glyceryl 1,3-palmitate-2-butyrate; glyceryl 1,3-stearate-2-caprate; glyceryl 1,2-linoleate-3-caprylate; glyceryl palmitostearate; and glyceryl behenate.

Fractionated triglycerides, modified triglycerides, synthetic triglycerides, fat-soluble vitamins, and mixtures of oils or triglycerides are also within the scope of the invention. Particularly preferred oils or triglycerides include vegetable oils, fish oils, animal fats, hydrogenated vegetable oils, partially hydrogenated vegetable oils, medium and long-chain triglycerides, structured triglycerides, and vitamin E and vitamin E derivatives such as tocopheryl acetate and tocopheryl acid succinate, and vitamin E analogues such as tocotrienols .

It should be appreciated that several commercial surfactant compositions contain small to moderate amounts of triglycerides, typically as a result of incomplete reaction of a triglyceride starting material in, for example, a transesterification reaction. Such commercial surfactant compositions, while nominally referred to as "surfactants", may be suitable to provide all or part of the triglyceride component for the compositions of the present invention. Examples of commercial surfactant compositions containing triglycerides include some members of the surfactant families Gelucires (Gattefosse), Maisines (Gattefosse), and Imwitors (Hüls). Specific examples of these compositions are as follows: Gelucire 44/14 (saturated polyglycolized glycerides); Gelucire 50/13 (saturated polyglycolized glycerides); Gelucire 53/10 (saturated polyglycolized glycerides); Gelucire 33/01 (semi-synthetic triglycerides of $C_8$–$C_1$ saturated fatty acids); Gelucire 39/01 (semi-synthetic glycerides); other Gelucires, such as 37/06, 43/01, 35/10, 37/02, 46/07, 48/09, 50/02, 62/05, etc.; Maisine 35-I (linoleic glycerides); and Imwitor 742 (caprylic/capric glycerides).

Other commercial surfactant compositions having significant triglyceride content are known to those skilled in the art and may serve as the carrier herein. It should be appreciated that such compositions, which contain triglycerides as well as surfactants, may be suitable to provide all or part of the triglyceride component of the compositions of the present invention, as well as all or part of the surfactant component, as described below.

Among the above-listed triglycerides (including surfactant compositions having significant triglyceride content), preferred triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially hydrogenated soy and cottonseed oil; glyceryl tricaproate; glyceryl tricaprylate; glyceryl triciaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate. Other preferred triglycerides are saturated polyglycolized glycerides (Gelucire 44/14, Gelucire 50/13 and Gelucire 53/10), linoleic glycerides (Maisine 35-I), and caprylic/capric glycerides (Imwitor 742).

Among these triglycerides, those that are particularly preferred are as follows: coconut oil; corn oil; olive oil; palm oil; peanut oil; safflower oil; sesame oil; soybean oil; hydrogenated castor oil; hydrogenated coconut oil; partially hydrogenated soybean oil; glyceryl tricaprate; glyceryl trilaurate; glyceryl trioleate; glyceryl trilinoleate; glyceryl tricaprylate/caprate; glyceryl tricaprylate/caprate/laurate; glyceryl tricaprylate/caprate/ linoleate; glyceryl tricaprylate/caprate/stearate; saturated polyglycolized glycerides (Gelucire 44/14, Gelucire 50/13 and Gelucire 53/10); linoleic glycerides (Maisine 35-I); and caprylic/capric glycerides (Imwitor 742).

As noted earlier herein, the carrier can also comprise a pharmaceutically acceptable surfactant. The surfactant may be hydrophilic or lipophilic. As is well known in the art, the terms "hydrophilic" and "lipophilic" or "hydrophobic" are relative terms. To function as a surfactant, a compound must necessarily include polar or charged hydrophilic moieties as well as non-polar lipophilic (hydrophobic) moieties; that is, a surfactant compound must be amphiphilic. An empirical parameter commonly used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10. It should be appreciated that the HLB value of a surfactant is merely a rough guide generally used to enable formulation of industrial, pharmaceutical and cosmetic emulsions. For many important surfactants, including several polyethoxylated surfactants, it has been reported that HLB values can differ by as much as about 8 HLB units, depending upon the empirical method chosen to determine the HLB value; see, e.g., Schott (1990) J. Pharm. Sci. 12(1):87–88. Likewise, for certain polypropylene oxide-containing block copolymers (e.g., the Pluronic® surfactants, from BASF Corp.), the HLB values may not accurately reflect the true physical chemical nature of the compounds. Finally, commercial surfactant products are generally not pure compounds, but are complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Keeping these inherent difficulties in mind, and using HLB values as a guide, one skilled in the art can readily identify surfactants having suitable hydrophilicity or hydrophobicity for use in the formulations of the present invention.

Suitable hydrophilic surfactants for use in the present formulations are any hydrophilic surfactants that are acceptable for use in pharmaceutical compositions. Such surfactants can be anionic, cationic, zwitterionic or non-ionic, although non-ionic hydrophilic surfactants are preferred. As discussed above, these non-ionic hydrophilic surfactants will generally have HLB values greater than about 10. Mixtures of hydrophilic surfactants are also within the scope of the invention. Similarly, suitable lipophilic surfactants for use in the present formulations are any lipophilic surfactants that are acceptable for use in pharmaceutical compositions. In general, suitable lipophilic surfactants will have an HLB value less than about 10. Mixtures of lipophilic surfactants are also within the scope of the invention.

The choice of specific lipophilic and hydrophilic surfactants for use in conjunction with the formulations of the invention should be made keeping in mind the particular bisphosphonic acid to be used in the composition, and the range of polarity appropriate for the chosen active agents, as discussed in more detail below. With these general principles in mind, a very broad range of surfactants is suitable for use in the formulations of the present invention. Surfactants useful herein include, but are not limited to, polyethylene glycol fatty acid esters, alcohol-oil transesterification products, polyglycerized fatty acids, propylene glycol fatty acid esters, mixtures of propylene glycol fatty acid esters and glycerol fatty acid esters, mono- and diglycerides, sterol and sterol derivatives, sorbitan fatty acid esters and polyethylene glycol sorbitan fatty acid esters, sugar esters, polyethylene glycol alkyl ethers and polyethylene glycol alkyl phenol ethers, polyoxyethylene-polyoxypropylene block copolymers, lower alcohol fatty acid esters, ionic surfactants, and ionizable surfactants, as follows.

Polyethylene Glycol Fatty Acid Esters: Although polyethylene glycol itself does not function as a surfactant, a variety of PEG-fatty acid esters, such as PEG-fatty acid monoester, PEG-fatty acid diesters, and PEG-fatty acid mono- and di-ester mixtures have useful surfactant properties. Among the PEG-fatty acid esters, esters of caproic acid, caprylic acid, capric acid, lauric acid, oleic acid, stearic acid, linoleic acid, and linolenic acid are especially useful.

Alcohol-Oil Transesterification Products: A large number of surfactants of different degrees of hydrophobicity or hydrophilicity can be prepared by reaction of alcohols or polyalcohols with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, maltol, sorbitol, and pentaerythritol. Among these alcohol-oil transesterified surfactants, preferred hydrophilic surfactants are PEG-35 castor oil (Incrocas-35), PEG-40 hydrogenated castor oil (Cremophor RH 40), PEG-25 trioleate (TAGAT® TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767). Preferred lipophilic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil® M 2735 CS), PEG-8 corn oil (Labrafil® WL 2609 BS), PEG-20 corn glycerides (Crovol M40), and PEG-20 almond glycerides (Crovol A40). The latter two surfactants are reported to have HLB values of ~10, which is generally considered to be the approximate border line between hydrophilic and hydrophobic surfactants. For purposes of the present invention, these two surfactants are considered to be hydrophobic. Also include as oils in this category of surfactants are oil-soluble vitamins, such as vitamins A, D, E, K, and their analogues and derivatives, etc. Thus, derivatives of these vitamins, such as tocopheryl PEG-1000 succinate (TPGS, available from Eastman), are also suitable surfactants.

Polyglycerized Fatty Acids: Among the polyglyceryl fatty acid esters, preferred hydrophilic surfactants include polyglyceryl-10 laurate (Nikkol Decaglyn 1-L), polyglyceryl-10 oleate (Nikkol Decaglyn 1-O), and polyglyceryl-10 mono, dioleate (Caprol® PEG 860). Preferred lipophilic surfactants include polyglyceryl oleate (Plurol Oleique), polyglyceryl-2 dioleate (Nikkol DGDO), and polyglyceryl-10 trioleate. Polyglyceryl polyricinoleates (Polymuls) are also preferred hydrophilic and lipophilic surfactants.

Propylene Glycol Fatty Acid Esters: Both mono- and diesters of propylene glycol may be used. In this surfactant class, preferred lipophilic surfactants include Capryol 90, Labrafac PG, propylene glycol monolaurate (Lauroglycol FCC), propylene glycol ricinoleate (Propymuls), propylene glycol monooleate (Myverol P-06), propylene glycol dicaprylate/dicaprate (Captex® 200), and propylene glycol dioctanoate (Captex® 800).

Mixtures of Propylene Glycol Fatty Acid Esters and Glycerol Fatty Acid Esters: In general, mixtures of surfactants are also suitable for use in the present invention. In particular, mixtures of propylene glycol fatty acid esters and glycerol fatty acid esters are suitable and are commercially available. One preferred mixture is composed of the oleic acid esters of propylene glycol and glycerol (Arlacel 186).

Mono- and Diglycerides: A particularly important class of surfactants are the mono- and diglycerides. These surfactants are generally lipophilic. Preferred lipophilic surfactants in this class of compounds include glyceryl monooleate (Peceol), glyceryl ricinoleate, glyceryl laurate, glyceryl dilaurate (Capmul® GDL), glyceryl dioleate (Capmul® GDO), glyceryl mono/dioleate (Capmul® GMO-K), glyceryl caprylate/caprate (Capmul® MCM), caprylic acid mono/diglycerides (Inmwitor®988), and mono- and diacetylated monoglycerides (Myvacet® 9–45).

Sterol and Sterol Derivatives: Sterols and derivatives of sterols are can be hydrophilic or hydrophobic. Preferred derivatives include polyethylene glycol derivatives, and a preferred hydrophobic surfactant in this class is cholesterol. Preferred hydrophilic surfactants in this class are PEG-24 cholesterol ether (Solulan C-24), PEG-30 cholestanol (Nikkol DHC), and phytosterol (GENEROL series, Henkel).

Sorbitan Fatty Acid Esters and Polyethylene Glycol Sorbitan Fatty Acid Esters: A variety of sorbitan esters of fatty acids are suitable surfactants for use in the present invention. Among these esters, preferred hydrophilic surfactants include PEG-sorbitan fatty acid esters, such as PEG-20 sorbitan monolaurate (Tween-20), PEG-20 sorbitan monopalmitate (Tween-40), PEG-20 sorbitan monostearate (Tween-60), and PEG-20 sorbitan monooleate (Tween-80). Among these esters, preferred lipophilic surfactants include sorbitan fatty acid esters and some polyethylene glycol sorbitan fatty acid esters, such as sorbitan monolaurate (Arlacel 20), sorbitan monopalmitate (Span-40), sorbitan monooleate (Span-80), sorbitan monostearate, and sorbitan tristearate.

Sugar Esters: Preferred hydrophilic or lipophilic surfactants in this class include sucrose monolaurate, sucrose monopalmitate, sucrose distearate/monostearate, and sucrose acetate isobutyrate.

Polyethylene Glycol Alkyl Ethers and Polyethylene Glycol Alkyl Phenol Ethers: Ethers of polyethylene glycol and alkyl alcohols or phenols are also suitable surfactants for use in the present invention. Preferred ethers include PEG-3 oleyl ether (Volpo 3), PEG-4 lauryl ether (Brij 30), and PEG-10-100 nonyl phenol (Triton X series Rohm & Haas).

Polyoxyethylene-Polyoxypropylene ("POE-POP") Block Copolymers: The POE-POP block copolymers are a unique class of polymeric surfactants. The unique structure of the surfactants, with hydrophilic POE and hydrophobic POP moieties in well-defined ratios and positions, provides a wide variety of surfactants that are suitable herein. These surfactants are available under various trade names, including Synperonic PE series (ICI); Pluronic(series (BASF), Emkalyx, Lutrol (BASF), Supronic, Monolan, Pluracare, and Plurodac. The generic term for these polymers is "poloxamer" (CAS 9003-11-6). These polymers have the formula

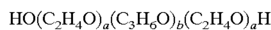

$$HO(C_2H_4O)_a(C_3H_6O)_b(C_2H_4O)_aH$$

where "a" and "b" denote the number of polyoxyethylene and polyoxypropylene units, respectively. Preferred hydrophilic surfactants of this class include Poloxamers 108, 188, 217, 238, 288, 338, and 407. Preferred hydrophobic surfactants in this class include Poloxamers 124, 182, 183, 212, 331, and 335.

Lower Alcohol Fatty Acid Esters: Esters of lower alcohols ($C_2$ to $C_4$) and fatty acids ($C_8$ to $C_{18}$) are suitable surfactants for use in the present formulations. Among these esters, preferred hydrophobic surfactants include ethyl oleate (Crodamol EO), isopropyl myristate (Crodamol IPM), and isopropyl palmitate (Crodamol IPP).

Ionic Surfactants: Ionic surfactants, including cationic, anionic and zwitterionic surfactants, may also be used. Preferred ionic surfactants include fatty acid salts, bile salts, phospholipids, carnitines, ether carboxylates, succinylated monoglycerides, mono/diacetylated tartaric acid esters of mono- and diglycerides, citric acid esters of mono-, diglycerides, alginate salts, and lactylic esters of fatty acids. Specifically, preferred ionic surfactants include sodium oleate, sodium lauryl sulfate, sodium lauryl sarcosinate, sodium dioctyl sulfosuccinate, sodium cholate, sodium taurocholate, lauroyl carnitine; palmitoyl carnitine; and myristoyl carnitine. It will be appreciated by one skilled in the art, however, that any bioacceptable counterion may be used. For example, although the fatty acids are shown as sodium salts, other cation counterions can also be used, such as alkali metal cations or ammonium. In contrast to typical non-ionic surfactants, these ionic surfactants are generally available as pure compounds.

Ionizable Surfactants: Ionizable surfactants, when present in neutral, uncharged form, are lipophilic (hydrophobic) surfactants suitable for use in the compositions and methods of the present invention, and in their ionized form, are hydrophilic surfactants suitable for use in the present invention. Particular examples of such surfactants include free fatty acids, particularly $C_6$–$C_{22}$ fatty acids, and bile acids. More specifically, suitable unionized ionizable surfactants include the free fatty acid and bile acid forms of any of the fatty acid salts and bile salts. Preferred ionizable surfactants include fatty acids and their corresponding salts, such as caprylic acid/sodium caprylate, oleic acid/sodium oleate, capric acid/sodium caprate; ricinoleic acid/sodium ricinoleate, linoleic acid/sodium linoleate, and lauric acid/sodium laurate; trihydroxy bile acids and their salts, such as cholic acid (natural), glycocholic acid and taurocholic acid; dihydroxy bile acids and their salts, such as deoxycholic acid (natural), glycodeoxycholic acid, taurodeoxycholic acid, chenodeoxycholic acid (natural), glycochenodeoxycholic acid, taurochenodeoxycholic acid, ursodeoxycholic acid, tauroursodeoxycholic acid, and glycoursodeoxycholic acid; monohydroxy bile acids and their salts, such as lithocholic acid (natural); sulfated bile salt derivatives; sarchocholate; fusidic acid and its derivatives; phospholipids, such as phosphatidyl choline, phosphatidyl ethanolamine, phosphatidyl serine, PD inositol, lysolecithin, and palmitoyl lysophosphatidyl choline; carnitines, such as palmitoyl camitine, lauroyl camitine and myristoyl carnitine; cyclodextrins, including alpha, beta and gamma cyclodextrins; and modified cyclodextrins, such as hydroxy propyl and sulfobutyl ether.

In addition to the carrier, the drug-containing formulation of the invention can further include pharmaceutically acceptable excipients or additives. Such additives include detackifiers, anti-foaming agents, buffering agents, polymers, antioxidants, preservatives, chelating agents, viscomodulators, tonicifiers, flavorants, colorants odorants, opacifiers, suspending agents, binders, fillers, plasticizers, lubricants, and mixtures thereof. The amounts of such additives can be readily determined by one skilled in the art, according to the particular properties desired.

It may be desirable to include one or more additional active agents in the dosage forms herein. A wide range of additional active agents may be co-administered with the bisphosphonic acid, including agents that potentiate certain effects of the bisphosphonic acid, or vice versa. Specifically, the additional active agent or agents can potentially enhance the inhibition of bone resorption by the bisphosphonic acid pharmacokinetically or pharmacodynamically, or can alleviate side effects associated with bisphosphonic acid adminstration, particularly esophageal irritation. Each of the additional active agents, like the bisphosphonic acid, may be in the form of a pharmaceutically acceptable salt, ester, amide, or other analog, derivative or prodrug, including active agents modified by appending one or more appropriate functionalities to enhance selected biological properties.

An acid or a base may be added to the composition to facilitate processing, or to prevent degradation of the hydrophilic therapeutic agent. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, and the like. Also suitable are bases which are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Preferred cations include sodium, potassium, lithium, magnesium, calcium and ammonium.

Suitable acids are pharmaceutically acceptable organic or inorganic acids. Examples of suitable inorganic acids include hydrochloric acid, hydrobromic acid, hyriodic acid, sulfuric acid, nitric acid, boric acid, phosphoric acid, and the like. Examples of suitable organic acids include acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

As noted earlier herein, the bisphosphonic acid formulation is contained within an enterically coated closed capsule. The capsule material may be either hard or soft, and as will be appreciated by those skilled in the art, typically comprises a tasteless, easily administered and water soluble compound such as gelatin, starch or a cellulosic material. The capsules are preferably sealed, such as with gelatin bands or the like. See, for example, *Remington: The Science and Practice of Pharmacy*, Nineteenth Edition (Easton, Pa.: Mack Publishing Co., 1995), which describes materials and methods for preparing encapsulated pharmaceuticals.

The enteric coating is typically although not necessarily a polymeric material. Preferred enteric coating materials comprise bioerodible, gradually hydrolyzable and/or gradually water-soluble polymers. The "coating weight," or relative amount of coating material per capsule, generally dictates the time interval between ingestion and drug release. Any coating should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery of the active to the lower gastrointestinal tract. The selection of the specific enteric coating material will depend on the following properties: resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; ease of application as a coating (substrate friendly); and economical practicality.

Suitable enteric coating materials include, but are not limited to: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropyhnethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl methacrylate (e.g., those copolymers sold under the tradename "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). Combinations of different coating materials may also be used to coat a single capsule. A particularly preferred enteric coating material for use herein are those acrylic acid polymers and copolymers available under the tradename "Eudragit" from Rohm Pharma (Germany). The Eudragit series E, L, S, RL, RS and NE copolymers are available as solubilized in organic solvent, as an aqueous dispersion, or as a dry powder. The Eudragit series RL, NE, and RS copolymers are insoluble in the gastrointestinal tract but are permeable and are used primarily for extended release. The Eudragit series E copolymers dissolve in the stomach. The Eudragit series L, L-30D and S copolymers are insoluble in stomach and dissolve in the intestine, and are thus most preferred herein.

A particularly suitable methacrylic copolymer is Eudragit L, particularly L-30D and Eudragit 100-55. In Eudragit L-30D, the ratio of free carboxyl groups to ester groups is approximately 1:1. Further, the copolymer is known to be insoluble in gastrointestinal fluids having pH below 5.5, generally 1.5–5.5, i.e., the pH generally present in the fluid of the upper gastrointestinal tract, but readily soluble or partially soluble at pH above 5.5, i.e., the pH generally present in the fluid of lower gastrointestinal tract. Another particularly suitable methacrylic acid polymer is Eudragit S, which differs from Eudragit L-30D in that the ratio of free carboxyl groups to ester groups is approximately 1:2. Eudragit S is insoluble at pH below 5.5, but unlike Eudragit L-30D, is poorly soluble in gastrointestinal fluids having a pH in the range of 5.5 to 7.0, such as in the small intestine. This copolymer is soluble at pH 7.0 and above, i.e., the pH generally found in the colon. Eudragit S can be used alone as a coating to provide drug delivery in the large intestine. Alternatively, Eudragit S, being poorly soluble in intestinal fluids below pH 7, can be used in combination with Eudragit L-30D, soluble in intestinal fluids above pH 5.5, in order to provide a delayed release composition which can be formulated to deliver the active agent to various segments of the intestinal tract. The more Eudragit L-30D used, the more proximal release and delivery begins, and the more Eudragit S used, the more distal release and delivery begins. It will be appreciated by those skilled in the art that both Eudragit L-30D and Eudragit S can be replaced with other pharmaceutically acceptable polymers having similar pH solubility characteristics.

The enteric coating provides for controlled release of the active agent, such that drug release can be accomplished at some generally predictable location in the lower intestinal tract below the point at which drug release would occur without the enteric coating. The enteric coating also prevents exposure of the hydrophilic therapeutic agent and carrier to the epithelial and mucosal tissue of the buccal cavity, pharynx, esophagus, and stomach, and to the enzymes associated with these tissues. The enteric coating therefore helps to protect the active agent and a patient's internal tissue from any adverse event prior to drug release at the desired site of delivery. Furthermore, the coated capsules of the present invention allow optimization of drug absorption, active agent protection, and safety. Multiple enteric coatings targeted to release the active agent at various regions in the lower gastrointestinal tract would enable even more effective and sustained improved delivery throughout the lower gastrointestinal tract.

The coating can, and usually does, contain a plasticizer to prevent the formation of pores and cracks that would permit the penetration of the gastric fluids. Suitable plasticizers include, but are not limited to, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating comprised of an anionic carboxylic acrylic polymer will usually contain approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

The coating can be applied to the capsule using conventional coating methods and equipment. For example, an enteric coating can be applied to a capsule using a coating pan, an airless spray technique, fluidized bed coating equipment, or the like. Detailed information concerning materials, equipment and processes for preparing coated dosage forms may be found in *Pharmaceutical Dosage Forms*: Tablets, eds. Lieberman et al. (New York: Marcel Dekker, Inc., 1989), and in Ansel et al., *Pharmaceutical Dosage Forms and Drug Delivery Systems*, 6$^{th}$ Ed. (Media, PA: Williams & Wilkins, 1995). The coating thickness, as noted above, must be sufficient to ensure that the oral dosage form remains intact until the desired site of topical delivery in the lower intestinal tract is reached.

B. Osmotically Activated Drug Delivery Devices

In another embodiment, drug dosage forms are provided that comprise an enterically coated, osmotically activated device housing a formulation of a bisphosphonic acid compound or a pharmacologically acceptable salt, hydrate or other derivative thereof, as described previously. The components of the internal, drug-containing formulation are as described above with respect to enterically coated capsules; however, conventional solid carriers can be used as well as the liquid and semi-solid carriers described in part (A).

In this embodiment, the drug-containing formulation is encapsulated in a semipermeable membrane or barrier containing a small orifice. As known in the art with respect to so-called "osmotic pump" drug delivery devices, the semipermeable membrane allows passage of water in either direction, but not drug. Therefore, when the device is exposed to aqueous fluids, water will flow into the device due to the osmotic pressure differential between the interior and exterior of the device. The flow rate of water into the device, dV/dt, can be represented as $$(kA/h)(\Delta\pi-\Delta P)$$

wherein k is the permeability of the membrane, A is the area of the membrane, h is the thickness of the membrane, $\Delta\pi$ is the osmotic pressure differential, and $\Delta P$ is the hydrostatic pressure differential. With a sufficiently large orifice, the osmotic pressure will be far greater than the hydrostatic pressure differential, so that the flow rate of water into the device may be represented simply as $$(kA/h)(\Delta\pi).$$

As water flows into the device, the drug-containing formulation in the interior will be "pumped" out through the orifice. The rate of drug release dD/dt, will be equivalent to the inflow rate of water times the drug concentration.

Suitable materials for the semipermeable membrane include, but are not limited to, polyvinyl alcohol, polyvinyl chloride, semipermeable polyethylene glycols, semipermeable polyurethanes, semipermeable polyamides, semipermeable sulfonated polystyrenes and polystyrene derivatives; semipermeable poly(sodium styrenesulfonate), semipermeable poly(vinylbenzyltrimethylammonium chloride), and cellulosic polymers such as cellulose acetate, cellulose diacetate, cellulose triacetate, cellulose propionate, cellulose acetate propionate, cellulose acetate butyrate, cellulose trivalerate, cellulose trilmate, cellulose tripalmitate, cellulose trioctanoate, cellulose tripropionate, cellulose disuccinate, cellulose dipalmitate, cellulose dicarpylate, cellulose acetate succinate, cellulose propionate succinate, cellulose acetate octanoate, cellulose valerate palmitate, cellulose acetate heptonate, cellulose acetaldehyde dimethyl acetate, cellulose acetate ethylcarbamate, cellulose acetate methylcarbamate, cellulose dimethylaminoacetate and ethyl cellulose.

Enterically coated, osmotically activated devices can be manufactured using conventional materials, methods and equipment. For example, osmotically activated devices may be made by first encapsulating, in a pharmaceutically acceptable soft capsule, a liquid or semi-solid formulation of a bisphosphonic acid compound as described previously. This interior capsule is then coated with a semipermeable membrane composition (comprising, for example, cellulose acetate and polyethylene glycol 4000 in a suitable solvent such as a methylene chloride-methanol admixture), for example using an air suspension machine, until a sufficiently thick laminate is formed, e.g., around 0.05 mm. The semipermeable laminated capsule is then dried using conventional techniques. Then, an orifice having a desired diameter (e.g., about 0.99 mm) is provided through the semipermeable laminated capsule wall, using, for example, mechanical drilling, laser drilling, mechanical rupturing, or erosion of an erodible element such as a gelatin plug. The osmotically activated device may then be enterically coated as previously described. For osmotically activated devices containing a solid carrier rather than a liquid or semi-solid carrier, the interior capsule is optional; that is, the semipermeable membrane may be formed directly around the carrier-drug composition. However, preferred carriers for use in the drug-containing formulation of the osmotically activated device are solutions, suspensions, liquids, immiscible liquids, emulsions, sols, colloids, and oils. Particularly preferred carriers include, but are not limited to, those described in Section IIA with respect to enterically coated capsules containing liquid or semisolid drug formulations.

III. Utility

The novel drug dosage forms are to be administered orally to a mammalian individual and can be used to administer a bisphosphonic acid compound as an active agent with minimal, if any, side effects. In accordance with the present invention, administration of a bisphosphonic acid compound may be carried out in order to treat any disorder, condition or disease for which such a compound is generally indicated. Such disorders, conditions and diseases include, for example, disturbances involving calcium or phosphate metabolism, e.g., involving bone resorption, particularly osteoporosis, Paget's disease, periprosthetic bone loss or osteolysis, malignant hypercalcemia, metastatic bone disease, multiple myeloma, periodontal disease, and tooth loss.

Dosage regimens and daily dosage for bisphosphonic acid compounds can vary a great deal, as a number of factors are involved, including the particular bisphosphonic acid used, age and general condition of the patient, the particular condition or disorder being treated, the severity of the patient's condition or disorder, and the like. Generally, however, the daily dose of a bisphosphonic acid compound will be in the range of about 0.1 mg to 500 mg, typically from about 5 mg to 100 mg, and most typically from about 5 mg to 60 mg.

For administration of alendronic acid, the typical daily dose is in the range of approximately 5 mg to 40 mg (corresponding to 6.53 to 52.21 mg alendronate, the monosodium salt trihydrate of alendronic acid), Currently, 5 mg/day is indicated for the prevention of osteoporosis, 10 mg/day for the treatment of osteoporosis, and 40 mg/day for the treatment of Paget's disease. For administration of etidronate sodium, 5 mg/kg/day to 20 mg/kg/day is indicated for the treatment of Paget's disease, while for administration of risedronate (in the form of anhydrous risedronate sodium), a daily dosage of about 20 mg to 40 mg, optimally 30 mg, is indicated for the treatment of Paget's disease. The daily dose of zdedronate, for treatment of tumor-induced hypercalemia, is generally in the range of 0.002 to 0.04 mg/kg.

It should be emphasized, however, that because the present dosage forms provide for substantially improved drug absorption relative to conventional formulations, it may not be necessary to administer the drug more than once every two to twelve weeks. Thus, in a preferred embodiment, a dosage form of the invention is administered to a patient every two weeks, preferably once a month, more preferably once every six weeks, most preferably every two months, and optimally every twelve weeks.

It is to be understood that while the invention has been described in conjunction with the preferred specific embodiments thereof, that the description above as well as the example which follows are intended to illustrate and not limit the scope of the invention. Other aspects, advantages and modifications within the scope of the invention will be apparent to those skilled in the art to which the invention pertains.

All patents, patent applications, and publications mentioned herein, both supra and infra, are hereby incorporated by reference.

EXPERIMENTAL

The practice of the present invention will employ, unless otherwise indicated, conventional techniques of pharmaceutical formulation, medicinal chemistry, biological testing, and the like, which are within the skill of the art. Such techniques are explained fully in the literature. Preparation of various types of pharmaceutical formulations are described, for example, in Lieberman et al., cited supra; and Gibaldi and Perrier, *Pharmacokinetics* (Marcel Dekker, 1982), provides a description of the testing procedures useful to evaluate drug delivery systems such as the enterically coated dosage forms described and claimed herein.

In the following example, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric. All reagents were obtained commercially unless otherwise indicated.

EXAMPLE 1

An enterically coated capsule for oral administration of bisphosphonic acid was prepared using standard mixing, encapsulation and coating techniques known to those skilled in the art. The bisphosphonic acid, carrier and optional additional components were first mixed to prepare the interior, drug/carrier formulation. The formulation was then encapsulated into a soft gelatin capsule, and the capsule coated with an aqueous dispersion of enteric coating components. The amount of coating resulted in a film of approximately 10 to 300 μm.

| | | mg/capsule |
|---|---|---|
| Active Agent: | Alendronate | 10 |
| Carrier Formulation: | Cremophor RH40 | 250 |
| | Labrasol | 100 |
| | Capmul ® MCM | 150 |
| Enteric Coating: | Eudragit ® L-100 | 18 |
| | Triacetin | 5 |
| | Talc | 1.5 |

EXAMPLE 2

An enterically coated capsule for oral administration of bisphosphonic acid, as set forth below, was prepared using the methodology of Example 1.

| | | mg/capsule |
|---|---|---|
| Active Agent: | Alendronate | 20 |
| Carrier Formulation: | Tween ® 20 | 320 |
| | Lauroglycol FCC | 100 |
| | Glycofurol | 80 |
| Enteric Coating: | Eudragit ® L-30D | 18 |
| | Propylene glycol | 5 |
| | Talc | 1.5 |

EXAMPLE 3

An enterically coated capsule for oral administration of bisphosphonic acid, as set forth below, was prepared using the methodology of Example 1.

| | | mg/capsule |
|---|---|---|
| Active Agent: | Alendronate | 60 |
| Carrier Formulation: | Cremophor ® RH40 | 300 |
| | Arlacel ® 186 | 200 |
| | Sodium taurocholate | 180 |
| | Propylene glycol | 320 |
| Enteric Coating: | Eudragit ® L-100 | 30 |
| | Triacetin | 5 |
| | Talc | 2 |

EXAMPLE 4

An enterically coated capsule for oral administration of bisphosphonic acid, as set forth below, was prepared using the methodology of Example 1.

| | | mg/capsule |
|---|---|---|
| Active Agent: | Alendronate | 20 |
| Carrier Formulation: | Cremophor ® RH40 | 250 |
| | Maisine ® 35-1 | 100 |
| | α-Tocopherol | 150 |
| Enteric Coating: | Eudragit ® L-100 | 30 |
| | Triacetin | 5 |
| | Talc | 2 |

EXAMPLE 5

An enterically coated capsule for oral administration of bisphosphonic acid, as set forth below, was prepared using the methodology of Example 1.

| | | mg/capsule |
|---|---|---|
| Active Agent: | Alendronate | 20 |
| Carrier Formulation: | Tween ® 20 | 600 |
| | Lauroglycol FCC | 330 |
| | Captex ® 350 | 70 |
| | Water* | 100 |
| Enteric Coating: | Eudragit ® L-100 | 30 |
| | Triacetin | 5 |
| | Talc | 2 |

*Water was removed from the capsule filling after the alendronate was dispersed evenly in the carrier formulation.

EXAMPLE 6

An enterically coated capsule for oral administration of bisphosphonic acid, as set forth below, was prepared using the methodology of Example 1.

| | | mg/capsule |
|---|---|---|
| Active Agent: | Alendronate | 20 |
| Carrier Formulation: | α-Tocopherol | 360 |
| | Labrafil ® M1944CS | 260 |
| | Crovol ® M40 | 200 |
| | Water* | 100 |
| Enteric Coating: | Eudragit ® L-100 | 30 |
| | Triacetin | 5 |
| | Talc | 2 |

*Water was removed from the capsule filling after the alendronate is dispersed evenly in the carrier formulation.

EXAMPLE 7

An enterically coated capsule for oral administration of bisphosphonic acid, as set forth below, was prepared using the methodology of Example 1.

| | | mg/capsule |
|---|---|---|
| Active Agent: | Alendronate | 10 |
| Carrier Formulation: | Cremophor RH40 | 250 |
| | Labrasol | 100 |
| | Capmul ® MCM | 150 |
| Enteric Coating: | Eudragit ® L-100 | 18 |
| | Triacetin | 5 |
| | Talc | 1.5 |

EXAMPLE 8

An enterically coated capsule for oral administration of bisphosphonic acid, as set forth below, was prepared using the methodology of Example 1.

| | | mg/capsule |
|---|---|---|
| Active Agent: | Alendronate | 10 |
| Carrier Formulation: | Cremophor RH40 | 352 |
| | Arlacel ® 186 | 315 |
| | Sodium Taurocholate | 135 |
| | Propylene Glycol | 225 |
| Enteric Coating: | Eudragit ® L-100 | 18 |
| | Triacetin | 5 |
| | Talc | 1.5 |

EXAMPLE 9

An enterically coated capsule for oral administration of bisphosphonic acid, as set forth below, was prepared using the methodology of Example 1.

| | | mg/capsule |
|---|---|---|
| Active Agent: | Alendronate | 10 |
| Carrier Formulation: | Cremophor ® RH40 | 360 |
| | Arlacel ® 186 | 340 |
| | Sodium Chenodeoxycholate | 135 |
| | Propylene Glycol | 225 |
| Enteric Coating: | Eudragit ® L-100 | 18 |
| | Triacetin | 5 |
| | Talc | 1.5 |

EXAMPLE 10

An enterically coated capsule for oral administration of bisphosphonic acid, as set forth below, was prepared using the methodology of Example 1.

| | | mg/capsule |
|---|---|---|
| Active Agent: | Alendronate | 10 |
| Carrier Formulation: | Tween ® 20 | 610 |
| | Lauroglycol FCC | 310 |
| | Captex ® | 60 |
| Enteric Coating: | Eudragit ® L-100 | 18 |
| | Triacetin | 5 |
| | Talc | 1.5 |

EXAMPLES 11–118

The procedure of Examples 1–10 may be employed with any number of bisphosphonic acids, carrier components and enteric coatings. These examples illustrate the wide variation in carrier components that may be used.

Accordingly, the procedure of Example 1 is repeated using 10 mg alendronate and an enteric coating comprised of 18 mg Eudragite® L-100, 5 mg triacetin and 1.5 mg talc, with the carrier formulations as set forth in the following table:

| Example No. | Carrier Components | mg/capsule |
|---|---|---|
| 11 | Sodium taurocholate | 180 |
| | Cremophor RH 40 | 300 |
| 12 | Sodium chenodeoxycholate | 300 |
| | Tween 80 | 500 |
| 13 | Sodium sarcocholate | 150 |
| | Crovol M-70 | 600 |
| 14 | Sodium lithocholate | 300 |
| | Labrasol | 550 |
| 15 | Sodium glycocholate | 100 |
| | Tween 20 | 500 |
| 16 | Sodium ursodeoxycholate | 300 |
| | Incrocas-35 | 500 |
| 17 | Chenodeoxycholic acid | 250 |
| | Cremophor RH40 | 500 |
| 18 | Cremophor RH40 | 600 |
| | Sodium caprate | 100 |
| 19 | Cremophor RH40 | 500 |
| | Palmitoyl carnitine | 200 |
| 20 | Solulan C-24 | 600 |
| | Sodium chenodeoxycholate | 250 |
| 21 | Sodium taurocholate | 200 |
| | Egg or soy lecithin | 90 |
| 22 | Tween 20 | 300 |
| | Sodium taurocholate | 200 |
| 23 | Tween 20 | 250 |
| | Egg lecithin | 150 |
| 24 | Sodium chenodeoxycholate | 180 |
| | $C_{18}$ lysolipid | 100 |
| 25 | Sodium chenodeoxycholate | 200 |
| | Oleic acid | 100 |
| 26 | Labrasol | 200 |
| | Brij 35 | 750 |
| 27 | Cremophor EL-P | 830 |
| | Propylene glycol monocaprate | 170 |
| 28 | Cremophor EL-P | 500 |
| | Imwitor 375 | 200 |
| 29 | Cremophor EL-P | 500 |
| | Nikkol MGM | 180 |
| 30 | Cremophor RH40 | 500 |
| | Arlacel 186 | 100 |
| 31 | Cremophor RH40 | 1530 |
| | Arlacel 186 | 380 |
| | HPB cyclodextrin | 180 |
| 32 | Cremophor RH40 | 500 |
| | Capmul MCM | 280 |
| 33 | Cremophor RH40 | 550 |
| | Crodamol (ethyl oleate) | 800 |
| 34 | Cremophor RH40 | 500 |
| | Labrafil | 400 |
| 35 | Cremophor RH40 | 220 |
| | Lauroglycol FCC | 200 |
| 36 | Cremophor RH40 | 600 |
| | Glyceryl monolaurate | 200 |
| 37 | Cremophor RH40 | 430 |
| | Myvacet 9-45 | 310 |
| 38 | Cremophor RH40 | 300 |
| | Peceol | 110 |
| 39 | Cremophor RH40 | 500 |
| | Propyleneglycol monooleate | 200 |
| 40 | Cremophor RH40 | 500 |
| | Softigen 701 | 100 |
| 41 | Cremophor RH40 | 500 |
| | Sorbitan monocaprate | 250 |
| 42 | Cremophor RH 60 | 540 |
| | Span 80 | 260 |
| 43 | Cremophor RH 40 | 700 |
| | Volpo 3 | 300 |

-continued

| Example No. | Carrier Components | mg/capsule |
|---|---|---|
| 44 | Crodet O40 | 680 |
| | Plurol Oleique | 320 |
| 45 | Crovol M-70 | 610 |
| | Crovol M-40 | 120 |
| 46 | Crovol M-70 | 380 |
| | Labrafil | 600 |
| 47 | Crovol M-70 | 650 |
| | Imwitor 988 | 150 |
| 48 | Crovol M-70 | 600 |
| | Linoleic acid | 200 |
| 49 | Emalex C-40 | 500 |
| | Gelucire 33/01 | 150 |
| 50 | Glycerox L | 730 |
| | Myvacet 9-45 | 270 |
| 51 | Incrocas 35 | 650 |
| | Arlacel 186 | 120 |
| 52 | Incrocas 35 | 250 |
| | Gelucire 44/14 | 150 |
| 53 | Incrocas 35 | 830 |
| | Imwitor 988 | 200 |
| 54 | Incrocas 35 | 310 |
| | Labrafil | 110 |
| 55 | Labrasol | 830 |
| | Lauroglycol | 170 |
| 56 | Lauroyl carnitine | 150 |
| | Imwitor 312 | 150 |
| 57 | Incrocas 35 | 500 |
| | Myvacet 9-45 | 380 |
| 58 | Incrocas-35 | 500 |
| | Span-20 | 150 |
| 59 | Incrocas 35 | 510 |
| | Imwitor 988 | 220 |
| 60 | Kessco PEG 300DL | 350 |
| | Gelucire 50/15 | 500 |
| 61 | Kessco PEG 1540DO | 650 |
| | Span 80 | 120 |
| 62 | Labrasol | 450 |
| | Span-20 | 250 |
| 63 | Myrj 44 | 500 |
| | Sorbitan monocaprylate | 250 |
| 64 | Myrj 52 | 500 |
| | Imwitor 308 | 200 |
| 65 | Sucrose monolaurate | 500 |
| | Capmul MCM | 200 |
| 66 | Nikkol Decaglyn 1-L | 550 |
| | Crovol M-40 | 330 |
| 67 | Nikkol Decaglyn 1-0 | 650 |
| | Capmul MCM | 250 |
| 68 | Nikkol DHC | 670 |
| | Nikkol TMGO-5 | 170 |
| 69 | Nikkol BPS-30 | 300 |
| | PEG-6 castor oil | 150 |
| 70 | Tween 20 | 750 |
| | Drewpol 6-1-0 | 150 |
| 71 | Tween 20 | 340 |
| | Lauroglycol FCC | 110 |
| 72 | Tween 20 | 580 |
| | Plurol Oleique | 210 |
| 73 | Tween 80 | 670 |
| | Lauroglycol | 170 |
| 74 | Tagat O2 | 500 |
| | PGMG-03 | 050 |
| 75 | Tagat L2 | 680 |
| | Brij 30 | 320 |
| 76 | Poloxamer 188 | 850 |
| | Labrafil M2125CS | 150 |
| 77 | Poloxamer 108 | 850 |
| | Capmul GMO-K | 150 |
| 78 | Solulan C-24 | 580 |
| | Lauroglycol FCC | 210 |
| 79 | Cremophor EL | 300 |
| | Labrasol | 300 |
| | Capmul MCM | 400 |
| 80 | Cremophor RH-40 | 250 |
| | Labrasol | 250 |
| | Capmul GMO-K | 110 |

-continued

| Example No. | Carrier Components | mg/capsule |
|---|---|---|
| 81 | Cremophor RH 40 | 300 |
| | Tween-20 | 200 |
| | Nikkol Decaglyn 3-O | 500 |
| 82 | Cremophor EL-P | 450 |
| | Corvol M-40 | 250 |
| | Sodium Docusate | 150 |
| 83 | Cremophor RH 40 | 650 |
| | Arlacel 186 | 150 |
| | Sodium dodecyl sulfate | 100 |
| 84 | Cremophor RH 40 | 500 |
| | Peceol | 200 |
| | Sodium docusate | 200 |
| 85 | Sodium Chenodeoxycholate | 300 |
| | Cremophor RH 40 | 400 |
| | Arlacel 186 | 300 |
| 86 | Cremophor RH 40 | 410 |
| | Sodium taurocholate | 260 |
| | Arlacel 186 | 270 |
| 87 | Cremophor RH 40 | 500 |
| | Softigen 767 | 220 |
| | Arlacel 186 | 150 |
| 88 | Cremophor RH 40 | 400 |
| | Arlacel 186 | 400 |
| | Tween 20 | 200 |
| 89 | Cremophor RH 40 | 350 |
| | Capmul MCM | 300 |
| | Sodium chenodeoxycholate | 300 |
| 90 | Kessco PEG 1000MO | 300 |
| | Labrasol | 300 |
| | Span 20 | 400 |
| 91 | Polaxamer 188 | 650 |
| | Peceol | 150 |
| | Sodium dodecyl sulfate | 100 |
| 92 | Sodium taurocholate | 170 |
| | Tween 20 | 660 |
| | Arlacel 186 | 170 |
| 93 | Sodium taurocholate | 170 |
| | Kessco PEG 1000MO | 660 |
| | Plurol Oleique | 170 |
| 94 | Sodium taurocholate | 150 |
| | Tween 80 | 180 |
| | Arlacel 186 | 180 |
| 95 | Taurochenodeoxycholate | 150 |
| | Tween 20 | 400 |
| | Arlacel 186 | 150 |
| 96 | Chenodeoxycholic acid | 250 |
| | Incrocas-35 | 300 |
| | Span 20 | 200 |
| 97 | Saurcocholate | 200 |
| | Cremophor RH 40 | 400 |
| | Arlacel 186 | 200 |
| 98 | Lithocholate | 250 |
| | Incrocas-35 | 400 |
| | Myvacet 9-45 | 300 |
| 99 | Tagat L2 | 450 |
| | Crovol A-40 | 250 |
| | Sodium docusate | 150 |
| 100 | Tween -20 | 300 |
| | Arlacel 186 | 200 |
| | Sodium chenodeoxycholate | 250 |
| 101 | Cremophor RH40 | 400 |
| | Tween-20 | 250 |
| | Sodium caprate | 250 |
| 102 | Cremophor RH40 | 400 |
| | Lauric acid | 200 |
| | Incrocas-35 | 300 |
| 103 | Cremophor RH 40 | 500 |
| | Labrafil M2125CS | 270 |
| | Crovol M-40 | 280 |
| 104 | Cremophor RH 40 | 1530 |
| | Arlacel 186 | 380 |
| | Peceol | 380 |
| | HPB beta cyclodextrin | 380 |
| 105 | Cremophor RH 40 | 550 |
| | Labrafil M2125 CS | 340 |
| | Span 80 | 200 |

-continued

| Example No. | Carrier Components | mg/capsule |
|---|---|---|
| 106 | Cremophor RH 40 | 500 |
| | Labrafil M2125 CS | 270 |
| | Crovol M-40 | 280 |
| 107 | Polaxamer 108 | 450 |
| | Span 20 | 250 |
| | Sodium docusate | 150 |
| | Ethyl oleate | 150 |
| 108 | Softigen 767 | 450 |
| | Imwitor 742 | 250 |
| | Sodium docusate | 150 |
| | Ethyl oleate | 150 |
| 109 | Soybean Oil | 080 |
| | Tween 20 | 200 |
| | Tween 80 | 800 |
| 110 | Captex 810D | 250 |
| | Incrocas 35 | 500 |
| | Tween 80 | 500 |
| 111 | Captex 810D | 200 |
| | Incrocas 35 | 670 |
| | Myvacet 9-45 | 330 |
| 112 | Corn Oil | 250 |
| | Cremophor RH40 | 750 |
| | Peceol | 150 |
| | Propylene Glyco | 100 |
| 113 | Corn Oil | 400 |
| | Cremophor RH40 | 570 |
| | Crovol M40 | 430 |
| 114 | Soybean Oil | 400 |
| | Cremophor RH40 | 570 |
| | Kessco PEG 400 MO | 430 |
| 115 | Captex 355 | 400 |
| | Tween 20 | 660 |
| | Brij 30 | 340 |
| 116 | Captex 355 | 200 |
| | Cremophor RH40 | 500 |
| | Labrafil M2125CS | 300 |
| | Ethanol | 100 |
| 117 | Captex 355 | 250 |
| | Incrocas 35 | 600 |
| | Labrafil M2125CS | 150 |
| 118 | Pureco 76 | 160 |
| | Cremophor RH40 | 480 |
| | Labrafil M2125CS | 160 |

What is claimed is:

1. A pharmaceutical formulation for oral administration, comprising:

an enterically coated capsule housing a substantially nonaqueous liquid or semi-solid composition comprised of: (a) a therapeutically effective amount of an active agent selected from bisphosphonic acids and pharmacologically acceptable salts, hydrates, and other derivatives thereof; and (b) a pharmaceutically acceptable, substantially nonaqueous liquid or semi-solid carrier in which the active agent is dissolved or suspended.

2. The formulation of claim 1, wherein the active agent has the structural formula (I)

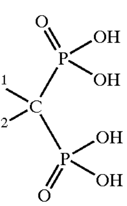

wherein $R^1$ is selected from the group consisting of hydrido, hydroxyl, alkoxy and halo, and $R^2$ is selected from the group consisting of halo, —$(CH_2)_m$—$NR^3R^4$, —$(CH_2)_n$—$R^5$, —O—$R^6$ and —S—$R^7$ wherein m is an integer in the range of zero to 8 inclusive, n is an integer in the range of 1 to 4 inclusive, $R^3$ and $R^4$ are independently hydrido or alkyl, or together form a $C_5$–$C_7$ cyclic group, and $R^5$, $R^6$ and $R^7$ are independently aryl and may be either unsubstituted or substituted with one or more substituents, or is a pharmacologically acceptable salt and/or hydrate thereof.

3. The formulation of claim 2, wherein $R^1$ is selected from the group consisting of hydrido, hydroxyl and halo, and $R^2$ is selected from the group consisting of halo, —$CH_2)_m$—$NR^3R^4$, —$CH_2)_n$—$R^5$ wherein $R^5$ is imidazolyl or pyridinyl, and —S—$R^7$ wherein $R^7$ is 4-chlorophenyl.

4. The formulation of claim 1, wherein the active agent is selected from the group consisting of alendronic acid, cimadronic acid, clodronic acid, etidronic acid, ibandronic acid, neridronic acid, olpadronic acid, pamidronic acid, piridronic acid, risedronic acid, tiludronic acid, zoledronic acid, and pharmacologically acceptable salts and hydrates thereof.

5. The formulation of claim 4, wherein the active agent is alendronic acid or a pharmacologically acceptable salt and/or hydrate thereof.

6. The formulation of claim 4, wherein the active agent is risedronic acid or a pharmacologically acceptable salt and/or hydrate thereof.

7. The formulation of claim 4, wherein the active agent is tiludronic acid or a pharmacologically acceptable salt and/or hydrate thereof.

8. The formulation of claim 4, wherein the active agent is zolendronic acid or a pharmacologically acceptable salt and/or hydrate thereof.

9. The formulation of claim 1, wherein the therapeutically effective amount is a unit dosage.

10. The formulation of claim 1, wherein the therapeutically effective amount is in the range of approximately 0.1 to 500 mg.

11. The formulation of claim 5, wherein the therapeutically effective amount is in the range of approximately 5 mg to 100 mg.

12. The formulation of claim 6, wherein the therapeutically effective amount is in the range of approximately 5 mg to 60 mg.

13. The formulation of claim 1, wherein the carrier comprises a solvent.

14. The formulation of claim 13, wherein the solvent is selected from the group consisting of alcohols, polyols, ethers, amides, esters, and mixtures thereof.

15. The formulation of claim 14, wherein the solvent is selected from the group consisting of triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol, glycofurol, diethylene glycol monoethyl ether, propylene glycol, sorbitol, glycerol, ethanol, dimethyl isosorbide, and mixtures thereof.

16. The formulation of claim 15, wherein the solvent is selected from the group consisting of sorbitol, glycerol, triacetin, ethanol, polyethylene glycol 400, glycofurol, propylene glycol, and mixtures thereof.

17. The formulation of claim 1, wherein the carrier comprises an oil, a triglyceride, or a mixture thereof.

18. The formulation of claim 17, wherein the carrier is selected from the group consisting of fractionated triglycerides, modified triglycerides, synthetic triglycerides, fat-soluble vitamins, and mixtures of oils or triglycerides.

19. The formulation of claim 17, wherein the carrier comprises a triglyceride.

20. The formulation of claim 17, wherein the carrier is selected from the group consisting of almond oil, babassu oil, borage oil, blackcurrant seed oil, canola oil, castor oil, coconut oil, corn oil, cottonseed oil, evening primrose oil, grapeseed oil, groundnut oil, mustard seed oil, olive oil, palm oil, palm kernel oil, peanut oil, rapeseed oil, safflower oil, sesame oil, shark liver oil, soybean oil, sunflower oil, hydrogenated castor oil, hydrogenated coconut oil, hydrogenated palm oil, hydrogenated soybean oil, hydrogenated vegetable oil, hydrogenated cottonseed and castor oil, partially hydrogenated soybean oil, partially hydrogenated soy and cottonseed oil, glyceryl tricaproate, glyceryl tricaprylate, glyceryl tricaprate, glyceryl triundecanoate, glyceryl trilaurate, glyceryl trioleate, glyceryl trilinoleate, glyceryl trilinolenate, glyceryl tricaprylate/caprate, glyceryl tricaprylate/caprate/laurate, glyceryl tricaprylate/caprate/linoleate, glyceryl tricaprylate/caprate/stearate, and mixtures thereof.

21. The formulation of claim 20, wherein the carrier is selected from the group consisting of coconut oil, corn oil, olive oil, palm oil, peanut oil, safflower oil, sesame oil, soybean oil, hydrogenated castor oil, hydrogenated coconut oil, partially hydrogenated soybean oil, glyceryl tricaprate, glyceryl trilaurate, glyceryl trioleate, glyceryl trilinoleate, glyceryl tricaprylate/caprate, glyceryl tricaprylate/caprate/laurate, glyceryl tricaprylate/caprate/linoleate, glyceryl tricaprylate/caprate/stearate, saturated polyglycolized glycerides, and mixtures thereof.

22. The formulation of claim 1, wherein the carrier comprises a surfactant.

23. The formulation of claim 22, wherein the surfactant is an anionic, cationic, zwitterionic or non-ionic surfactant.

24. The formulation of claim 23, wherein the surfactant is a hydrophilic surfactant.

25. The formulation of claim 22, wherein the surfactant is selected from the group consisting of polyethylene glycol fatty acid esters, alcohol-oil transesterification products, polyglycerized fatty acids, propylene glycol fatty acid esters, mixtures of propylene glycol fatty acid esters and glycerol fatty acid esters, mono- and diglycerides, sterol and sterol derivatives, sorbitan fatty acid esters and polyethylene glycol sorbitan fatty acid esters, sugar esters, polyethylene glycol alkyl ethers and polyethylene glycol alkyl phenol ethers, polyoxyethylene-polyoxypropylene block copolymers, lower alcohol fatty acid esters, ionic surfactants, and ionizable surfactants.

26. The formulation of claim 1, wherein the capsule is a gelatin, starch or cellulosic capsule.

27. The formulation of claim 1, further comprising an additional active agent.

28. The formulation of claim 1, wherein the enteric coating is comprised of a bioerodible, gradually hydrolyzable and/or gradually water-soluble coating.

29. The formulation of claim 28, wherein the enteric coating is comprised of a cellulosic polymer.

30. The formulation of claim 29, wherein the cellulosic polymer is selected from the group consisting of hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate, carboxymethylcellulose sodium, and mixtures thereof.

31. The formulation of claim 28, wherein the enteric coating is comprised of an acrylic acid polymer.

32. The formulation of claim 31, wherein the acrylic acid polymer is a copolymer of acrylic acid, methacrylic acid, methyl acrylate, ammonio methylacrylate, ethyl acrylate, methyl methacrylate and/or ethyl methacrylate.

33. The formulation of claim 28, wherein the enteric coating is comprised of a vinyl polymer selected from the group consisting of polyvinyl pyrrolidone, polyvinyl acetate, polyvinylacetate phthalate, vinylacetate crotonic acid copolymer, and ethylene-vinyl acetate copolymers.

34. The formulation of claim 28, wherein the enteric coating is comprised of purified lac.

35. The formulation of claim 1, wherein the capsule is coated with a single enteric coating layer.

36. The formulation of claim 1, wherein the capsule is coated with two or more enteric coating layers.

37. A method for treating a patient having a condition that is responsive to administration of an active agent selected from bisphosphonic acids and pharmacologically acceptable salts, hydrates and other derivatives thereof, comprising orally administering to the patient, within the context of an effective dosing regimen, the pharmaceutical formulation of claim 1.

38. The method of claim 37, wherein the condition involves calcium or phosphate metabolism.

39. The method of claim 38, wherein the condition involves bone resorption.

40. The method of claim 39, wherein the condition is osteoporosis, Paget's disease, periprosthetic bone loss, osteolysis, malignant hypercalcemia, metastatic bone disease, multiple myeloma, or periodontal disease.

41. The method of claim 37, wherein the formulation is administered once every two weeks.

42. The method of claim 37, wherein the formulation is administered once a month.

43. The method of claim 37, wherein the formulation is administered once every six weeks.

44. The method of claim 37, wherein the formulation is administered once every two months.

45. The method of claim 37, wherein the formulation is administered once every three months.

46. A The formulation of claim 1, wherein the carrier is selected to provide enhanced absorption of the active agent following oral administration of the capsule to a patient.

47. The formulation of claim 1, wherein the enteric coating is comprised of a polymeric material selected to provide resistance to degradation of the capsule and/or a decrease in the release or exposure of the active agent in the upper gastrointestinal tract, and/or a decrease in the release or exposure of the drug in the upper gastrointestinal tract.

48. A pharmaceutical formulation for oral administration, comprising:

an enterically coated capsule housing a liquid or semi-solid composition comprised of: (a) a therapeutically effective amount of an active agent selected from bisphosphonic acids and pharmacologically acceptable salts, hydrates, and other derivatives thereof and (b) a pharmaceutically acceptable, liquid or semi-solid carrier in which the active agent is dissolved or suspended, said carrier comprising (i) at least one surfactant selected from polyethylene glycol fatty acid esters, alcohol-oil transesterification products, polyglycerized fatty acids, propylene glycol fatty acid esters, mixtures of propylene glycol fatty acid esters and glycerol fatty acid esters, mono- and diglycerides, sterol and sterol derivatives, sorbitan fatty acid esters and polyethylene glycol sorbitan fatty acid esters, sugar esters, polyethylene glycol alkyl ethers and polyethylene glycol alkyl phenol ethers, polyoxyethylene-polyoxypropylene block copolymers, lower alcohol fatty acid esters, ionic surfactants, and ionizable surfactants, (ii) optionally, at least one triglyceride selected from oils, fractionated triglycerides, modified triglycerides, synthetic triglycerides, and soluble vitamins, and (iii) optionally, at least one organic solvent.

49. The formulation of claim 48, wherein the carrier is selected to provide enhanced absorption of the active agent following oral administration of the capsule to a patient.

50. The formulation of claim 48, wherein the enteric coating is comprised of a polymeric material selected to provide resistance to degradation of the capsule and/or a decrease in the release or exposure of the active agent in the upper gastrointestinal tract, and/or a decrease in the release or exposure of the drug in the upper gastrointestinal tract.

51. A method for treating a patient having a condition that is responsive to administration of an active agent selected from bisphosphonic acids and pharmacologically acceptable salts, hydrates and other derivatives thereof, comprising orally administering to the patient, within the context of an effective dosing regimen, the pharmaceutical formulation of claim 48.

52. The method of claim 51, wherein the condition involves calcium or phosphate metabolism.

53. The method of claim 52, wherein the condition involves bone resorption.

54. The method of claim 53, wherein the condition is osteoporosis, Paget's disease, periprosthetic bone loss, osteolysis, malignant hypercalcemia, metastatic bone disease, multiple myeloma, or periodontal disease.

55. The method of claim 51, wherein the formulation is administered once every two weeks.

56. The method of claim 51, wherein the formulation is administered once a month.

57. The method of claim 51, wherein the formulation is administered once every six weeks.

58. The method of claim 51, wherein the formulation is administered once every two months.

59. The method of claim 51, wherein the formulation is administered once every three months.

* * * * *

UNITED STATES PATENT AND TRADEMARK OFFICE

CERTIFICATE OF CORRECTION

PATENT NO. : 6,468,559 B1
DATED : October 22, 2002
INVENTOR(S) : Feng-Jing Chen and Mahesh V. Patel It is certified that error appears in the above-identified patent and that said Letters Patent is hereby corrected as shown below:

Title page,
Item [54], please change "BISHOSPHONIC" to -- BISPHOSPHONIC --.

Signed and Sealed this

Eighteenth Day of February, 2003

JAMES E. ROGAN
*Director of the United States Patent and Trademark Office*